United States Patent
Klein et al.

(10) Patent No.: US 11,507,749 B2
(45) Date of Patent: Nov. 22, 2022

(54) CONFIGURATION FOR PROVIDING A SERVICE THROUGH A MOBILE LANGUAGE INTERPRETATION PLATFORM

(71) Applicant: Language Line Services, Inc., Monterey, CA (US)

(72) Inventors: Scott W. Klein, Carmel, CA (US); Jeffrey Cordell, Carmel, CA (US); Lindsay D'Penha, Carmel, CA (US)

(73) Assignee: Language Line Services, Inc., Monterey, CA (US)

( * ) Notice: Subject to any disclaimer, the term of this patent is extended or adjusted under 35 U.S.C. 154(b) by 413 days.

(21) Appl. No.: 16/680,105

(22) Filed: Nov. 11, 2019

(65) Prior Publication Data
US 2021/0141864 A1    May 13, 2021

(51) Int. Cl.
| | | |
|---|---|---|
| *G06F 21/32* | (2013.01) | |
| *G06Q 50/22* | (2018.01) | |
| *G06F 40/30* | (2020.01) | |
| *G06F 3/16* | (2006.01) | |
| *G16H 10/60* | (2018.01) | |
| *G05D 1/00* | (2006.01) | |
| *G16H 40/20* | (2018.01) | |
| *G06V 30/416* | (2022.01) | |
| *H04L 67/12* | (2022.01) | |

(52) U.S. Cl.
CPC ........... *G06F 40/30* (2020.01); *G05D 1/0088* (2013.01); *G06F 3/167* (2013.01); *G06V 30/416* (2022.01); *G16H 10/60* (2018.01); *G16H 40/20* (2018.01); *H04L 67/12* (2013.01)

(58) Field of Classification Search
CPC ....... G06F 40/30; G06F 3/167; G05D 1/0088; G06V 30/416; G06V 30/40; G16H 10/60; G16H 40/20; G16H 40/63; G16H 40/67; H04L 67/12
See application file for complete search history.

(56) References Cited

U.S. PATENT DOCUMENTS

| | | | | |
|---|---|---|---|---|
| 2007/0050306 A1* | 3/2007 | McQueen | .............. | G06Q 20/14 705/77 |
| 2012/0035908 A1* | 2/2012 | Lebeau | .................... | G06F 40/40 704/E11.001 |

(Continued)

*Primary Examiner* — Maroun P Kanaan
(74) *Attorney, Agent, or Firm* — Patent Ingenuity, P.C.; Samuel K. Simpson

(57) ABSTRACT

A mobile language interpretation platform has a mobile support device. Further, the mobile language interpretation platform has one or more wheels attached to the mobile support device. Moreover, the mobile language interpretation platform has a computing device operably attached to the mobile support device. The computing device has a receiver that receives, from a context-specific server, a request for a context-specific service pertaining to a contextual environment in which the mobile language interpretation platform is physically located. Additionally, the computing device has a processor that performs the context-specific service and establishes a language interpretation session between at least one user situated at the mobile language interpretation platform and a remotely-situated language interpreter. Finally, the computing device has a transmitter that sends data pertaining to the context-specific service to the context-specific server.

20 Claims, 10 Drawing Sheets

(56) References Cited

U.S. PATENT DOCUMENTS

| | | | | |
|---|---|---|---|---|
| 2015/0173843 A1* | 6/2015 | Maughan | ............ | G06Q 10/087 |
| | | | | 705/3 |
| 2015/0223891 A1* | 8/2015 | Miller | .................... | A61B 50/13 |
| | | | | 726/19 |
| 2015/0302539 A1* | 10/2015 | Mazar | .................... | G08B 21/02 |
| | | | | 705/3 |
| 2017/0361468 A1* | 12/2017 | Cheuvront | ................ | G06F 3/01 |

* cited by examiner

CONFIGURATION FOR PROVIDING A SERVICE THROUGH A MOBILE LANGUAGE INTERPRETATION PLATFORM

BACKGROUND

1. Field

This disclosure generally relates to the field of language interpretation. More particularly, the disclosure relates to non-language interpretation services provided by a mobile language interpretation platform.

2. General Background

Conventional language interpretation configurations typically include a plurality of users with one or more communication devices (e.g., landline telephone, smartphone, tablet device, smartwatch, etc.), which may be used to connect to a language interpreter. For instance, a first human user, who speaks a first human-spoken language (i.e., a language that is traditionally spoken by a group of people originating from a particular geographical location, country, or region) such as English, may want to have a voice-based conversation in-person with a second human user, who speaks a second human-spoken language. As an example, an English speaker and a Spanish speaker may want to have a conversation, while both being in the same physical location.

Such language interpretation configurations are typically focused on providing a language interpretation service. For example, an over the phone interpretation ("OPI") session may be established via one or more voice-based interactive menus that presented to the one or more communication devices. As a result, language interpretation configurations are typically limited in applicability to language interpretation services.

SUMMARY

A mobile language interpretation platform has a mobile support device. Further, the mobile language interpretation platform has one or more wheels attached to the mobile support device. Moreover, the mobile language interpretation platform has a computing device operably attached to the mobile support device. The computing device has a receiver that receives, from a context-specific server, a request for a context-specific service pertaining to a contextual environment in which the mobile language interpretation platform is physically located. Additionally, the computing device has a processor that performs the context-specific service and establishes a language interpretation session between at least one user situated at the mobile language interpretation platform and a remotely-situated language interpreter. Finally, the computing device has a transmitter that sends data pertaining to the context-specific service to the context-specific server.

As another alternative, a computer program may have a computer readable storage device with a computer readable program stored thereon that implements the functionality of the aforementioned platform. As yet another alternative, a process that utilizes a processor may implement the functionality of the aforementioned platform.

BRIEF DESCRIPTION OF THE DRAWINGS

The above-mentioned features of the present disclosure will become more apparent with reference to the following description taken in conjunction with the accompanying drawings wherein like reference numerals denote like elements and in which.

DETAILED DESCRIPTION

A computerized configuration provides a context-specific service, possibly being related to language interpretation or not, through a mobile language interpretation platform. In essence, the mobile language interpretation platform is capable of moving to and from various locations within a particular contextual environment (e.g., a hospital) to provide both a language interpretation service and a context-specific service (e.g., a service directly related to the hospital context). For example, in the hospital context, the mobile language interpretation platform may provide a variety of additional services specific to the medical field (e.g., self-automated driving to a patient's location within the hospital, patient identification, electronic medical record ("EMR") generation, patient data analytics, etc.). Accordingly, the computerized configuration allows the mobile language interpretation platform to provide additional features to that of conventional language interpretation, thereby providing a synergistic solution that encompasses context-specific services in addition to language interpretation services.

In one embodiment, the computerized configuration is an IoT configuration that automatically performs computer-to-computer interactions without any human inputs. In another embodiment, the computerized configuration may be a partial IoT configuration that involves both computer-to-computer interactions and human-to-computer interactions. Finally, in yet another embodiment, the computerized configuration may be a human-to-computer configuration.

Figure 1:
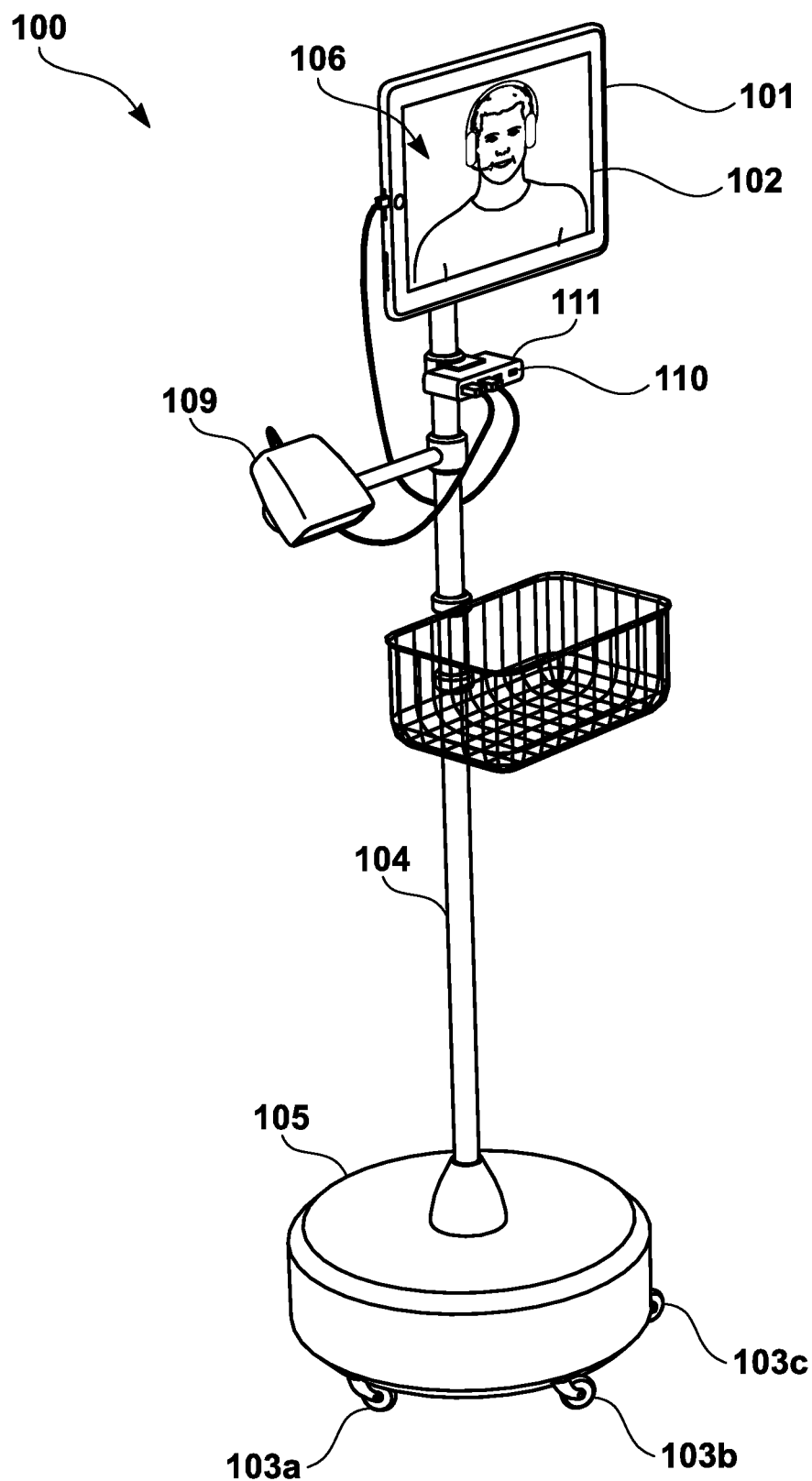
FIG. 1 Illustrates a mobile language interpretation platform that may be used to provide both a language interpretation service and a context-specific service.

FIG. 1 Illustrates a mobile language interpretation platform 100 that may be used to provide both a language interpretation service and a context-specific service. The mobile language interpretation platform 100 may have a mobile support device 104 (e.g., rod or other supporting structure) that maintains a position of a computing device 101 (e.g., personal computer, laptop computer, tablet device, smartphone, etc.). Furthermore, the mobile language interpretation platform 100 may have one or more wheels 103*a-c* that allow the mobile language interpretation platform 100 to be mobilized from one location to another. In one embodiment, the mobile language interpretation platform 100 has a motor, which allows for electronic mobilization of the mobile language interpretation platform 100 via the one or more wheels 103*a-c*, encapsulated by a housing 105. In another embodiment, the mobile language interpretation platform 100 does not have a motor, and is mobilized via human operation.

Additionally, the computing device 101 may have a display screen 102, which displays a GUI 106. As an example, the GUI 106 may depict a video remote interpretation ("VRI") session for language interpretation. A user situated in front of the computing device may communicate with a remotely situated language interpreter. Different forms of language interpretation (e.g., human spoken-language interpretation, American sign language ("ASL"), British sign language ("BSL"), etc.) may be performed via a language interpretation session established between the computing device 101 and a remotely-situated computing device over a computerized network.

Moreover, the mobile language interpretation platform 100 may have one or more connectors 110 (e.g., USB ports), arranged via a connector box 111, operably attached to the mobile support device 104. The one or more connectors 110 may be connect the computing device 101 to one or more I/O devices 109 such as a scanner, which may be used to obtain data from a user prior to, during, or after a language interpretation session.

Figure 2:
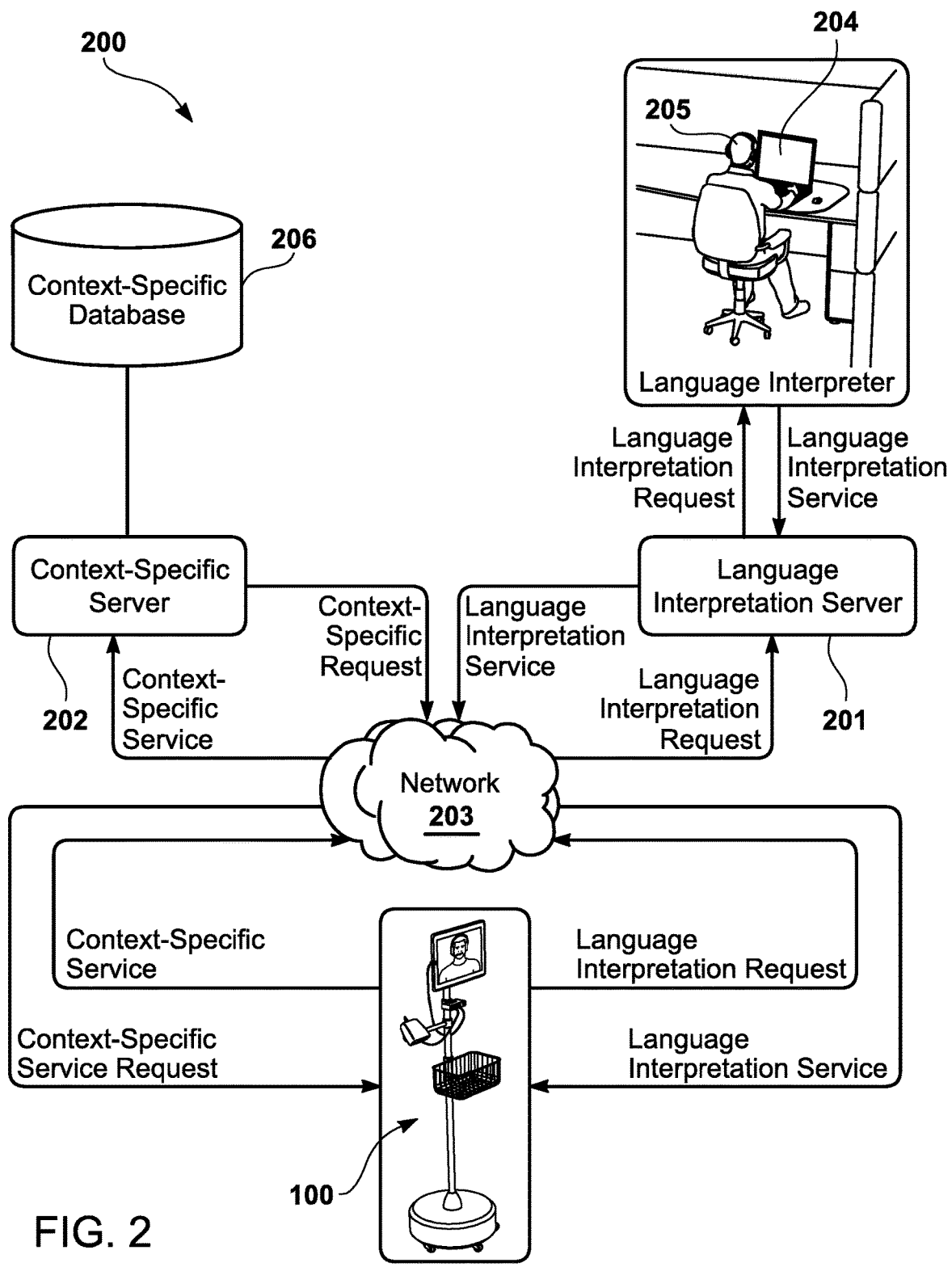
FIG. 2 illustrates a context-specific service configuration that may be implemented with the mobile language interpretation platform illustrated in FIG. 1.

FIG. 2 illustrates a context-specific service configuration 200 that may be implemented with the mobile language interpretation platform 100 illustrated in FIG. 1. The mobile language interpretation platform 100 may communicate, via a network 203, with a language interpretation server 201 to establish a language interpretation session. For instance, the mobile language interpretation platform 100 may send a request for a language interpretation session through the network 203 to the language interpretation server 201, which is in operable communication with a language interpreter 205 situated at a language interpreter communication device 204. Accordingly, the language interpretation server 201 may establish a language interpretation session between one or more users positioned at the mobile language interpretation platform 100 and the language interpreter positioned at the language interpreter communication device 204.

Furthermore, the mobile language interpretation platform 100 may communicate with a context-specific server 202 (e.g., a medical services server that provides service for a hospital in which the mobile language interpretation platform 100 is physically positioned) via the network 203. The context-specific server 202 may request that the mobile language interpretation platform 100 perform a variety of services, which may not be directly related to that of providing language interpretation services. For example, in the medical context, the context-specific server 202 may send instructions to the mobile language interpretation platform 100 to automatically control its movement to and from various destinations within a hospital. As another example, the context-specific server 202 may instruct the mobile language interpretation platform 100 to use the I/O device 109, illustrated in FIG. 1, to obtain various data (e.g., scan patient identification data, medical charts, etc.). The context-specific server 202 may store the various data obtained from the mobile language interpretation platform 100 in a context-specific database 206.

In one embodiment, the language interpretation server 201 and the context-specific server 202 are distinct servers that may perform their corresponding functionalities without communication with each other. In another embodiment, the language interpretation server 201 and the context-specific server 202 communicate with each other to perform context-specific services in conjunction with language interpretation services.

Figure 3:
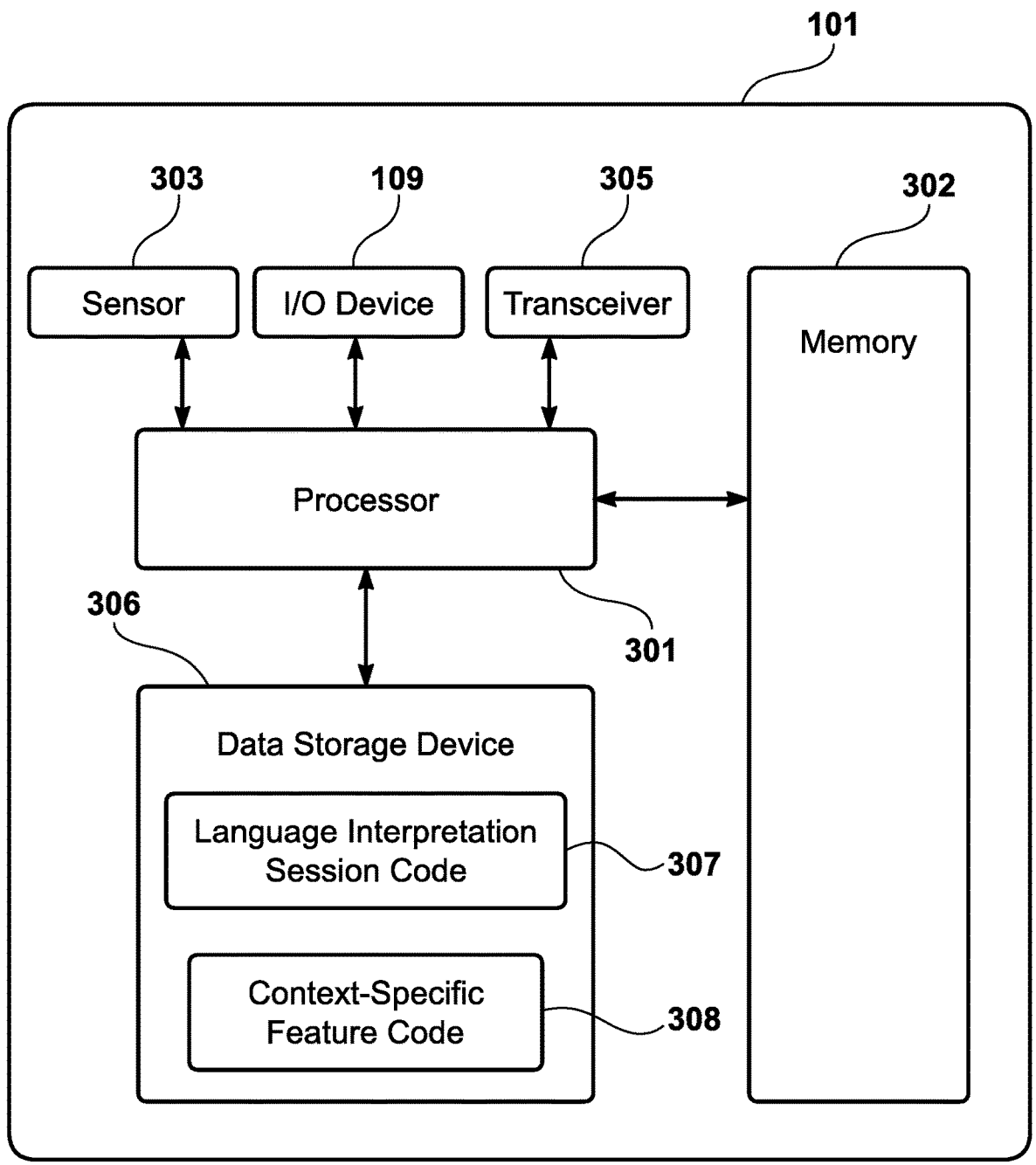
FIG. 3 illustrates a configuration of the internal components of the computing device illustrated in FIG. 1.

FIG. 3 illustrates a configuration of the internal components of the computing device 101 illustrated in FIG. 1. The computing device 101 has a processor 301, which may be specialized for generating language interpretation sessions in conjunction with context-specific services. For example, the processor 301 may have specialized graphics capability for displaying a high-quality VRI session, while also having significant processing power for transmitting and receiving context-specific data in real-time.

Furthermore, the processor 301 may retrieve various code from a data storage device 306 for execution in a memory device 302. For example, the processor 301 may retrieve language interpretation session code 307 from the data storage device 306 to establish a language interpretation session (e.g., a VRI session, an OPI session, etc.). As another example, the processor 301 may retrieve the context-specific feature code 308 to provide context-specific features distinct from, or in conjunction with, a language interpretation session.

Also, the computing device 101 may have a sensor 303 (e.g., GPS device, thermometer, etc.) that is used to sense data with respect to the mobile language interpretation platform 100 and/or a user situated at the mobile language interpretation platform 100. Further, the computing device 101 may also have the I/O device 109 (e.g., microphone, camera, scanner, etc.) that may be used to obtain data from the user and/or the surrounding contextual environment. Finally, the computing device 101 may have a transceiver 305 that is used to send and/or receive data through the network 203. (Alternatively, a separate transmitter and receiver may be used instead.)

The components described with respect to the computing device 101 may be used in addition to, or in the alternative, as components for the language interpretation server 201 and/or the context-specific server 202.

Figure 4A:
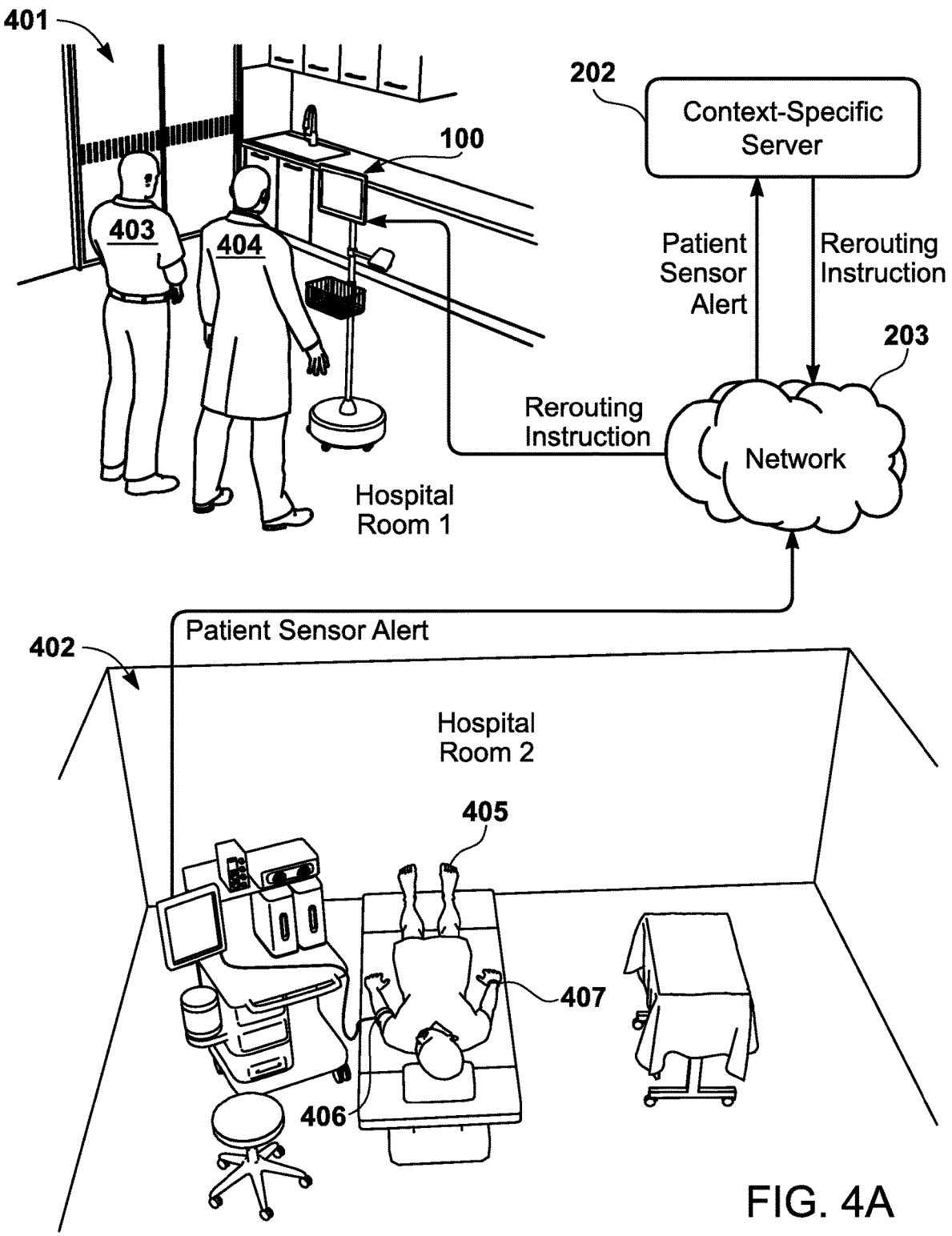
FIG. 4A illustrates an example of an Internet of Things ("IoT") based configuration in a contextual environment of a hospital.

FIGS. 4A-4E illustrate a variety of examples of context-specific services provided by the computing device 101 of the mobile language interpretation platform 100 illustrated in FIG. 1. In particular, FIG. 4A illustrates an example of an IoT-based configuration in a contextual environment of a hospital. The mobile language interpretation platform 100 may be initially positioned within a first hospital room 401 in which a limited English proficiency ("LEP") patient 403, who speaks Spanish, and a doctor 404, who speaks English, are in need of a language interpreter. Accordingly, the computing device 101 of the mobile language interpretation platform 100 may be used to establish a VRI session between the doctor 404 and the LEP patient 403.

However, a second patient 405 in a second hospital room 402 may have a sensor 406 (e.g., blood pressure monitor), which sends an alert, via the network 203, to the context-specific server 202. As a result, the context-specific server 202, and/or the language interpretation server 201, may send a rerouting instruction via the network 203 to the mobile language interpretation platform 100 to reroute the mobile language interpretation platform 100 from the first hospital room 401 to the second hospital room 402. In one embodiment, the context-specific server 202 prioritizes the alert, and interrupts the language interpretation session being performed within the first hospital room 401 to immediately reroute the mobile language interpretation platform 100. In another embodiment, the context-specific server 202 awaits completion of the language interpretation session before sending the instruction for the mobile language interpretation platform 100 to be rerouted to the second hospital room 402.

In one embodiment, the mobile language interpretation platform 100 automatically, and/or autonomously, mobilizes (e.g., via the motor) from the first hospital room 401 to the second hospital room 402. In another embodiment, the mobile language interpretation platform 100 may display a message via the display screen 102 of the computing device 101; the message indicating to a user that the mobile language interpretation platform 100 should be rerouted to the second hospital room 402.

Figure 4B:
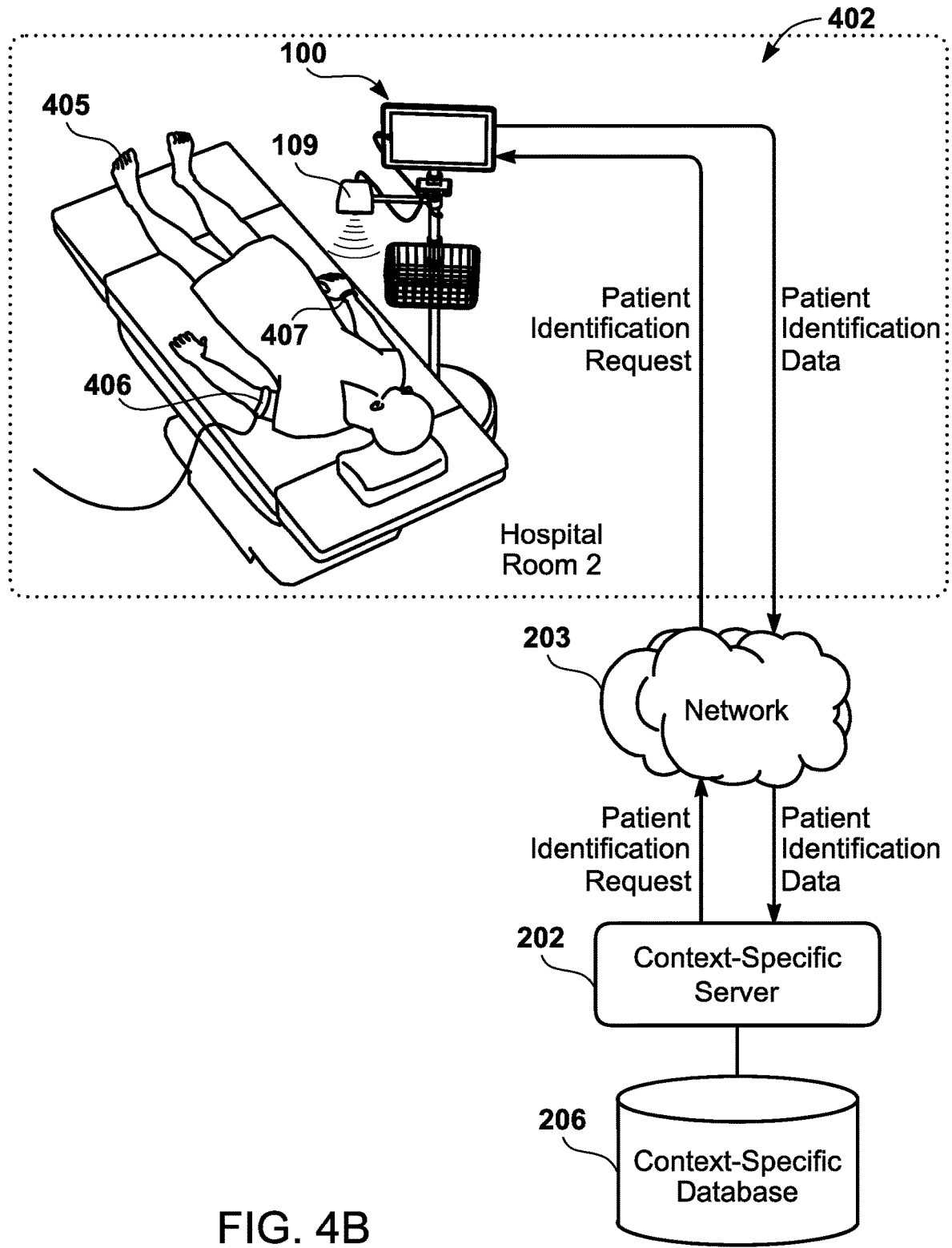
FIG. 4B illustrates an example of the mobile language interpretation platform using the input/output ("I/O") device to obtain data from the second patient in the second hospital room.

FIG. 4B illustrates an example of the mobile language interpretation platform 100 using the I/O device 109 to obtain data from the second patient 405 in the second hospital room 402. For example, the second patient 405 may be wearing an identification bracelet 407, on which a code (e.g., bar code, QR code, etc.) identifying the patient is displayed. (Other forms of patient identification (e.g., radio frequency identification ("RFID") tags may be used instead.) The mobile language interpretation platform 100 may be configured to automatically, without human intervention, position itself within the second hospital room 402 in proximity to the second patient 405 and scan the code on the identification bracelet 407. (Various computer vision techniques may be used for the computing device 101 to determine the location of the second patient 405 within the second hospital room 402.)

The mobile language interpretation platform 100 may then send the patient identification data, via the network 203, to the context-specific server 202, which may determine the identity of the second patient 405 via database retrieval from the context-specific database 206, as illustrated in FIG. 2.

Figure 4C:
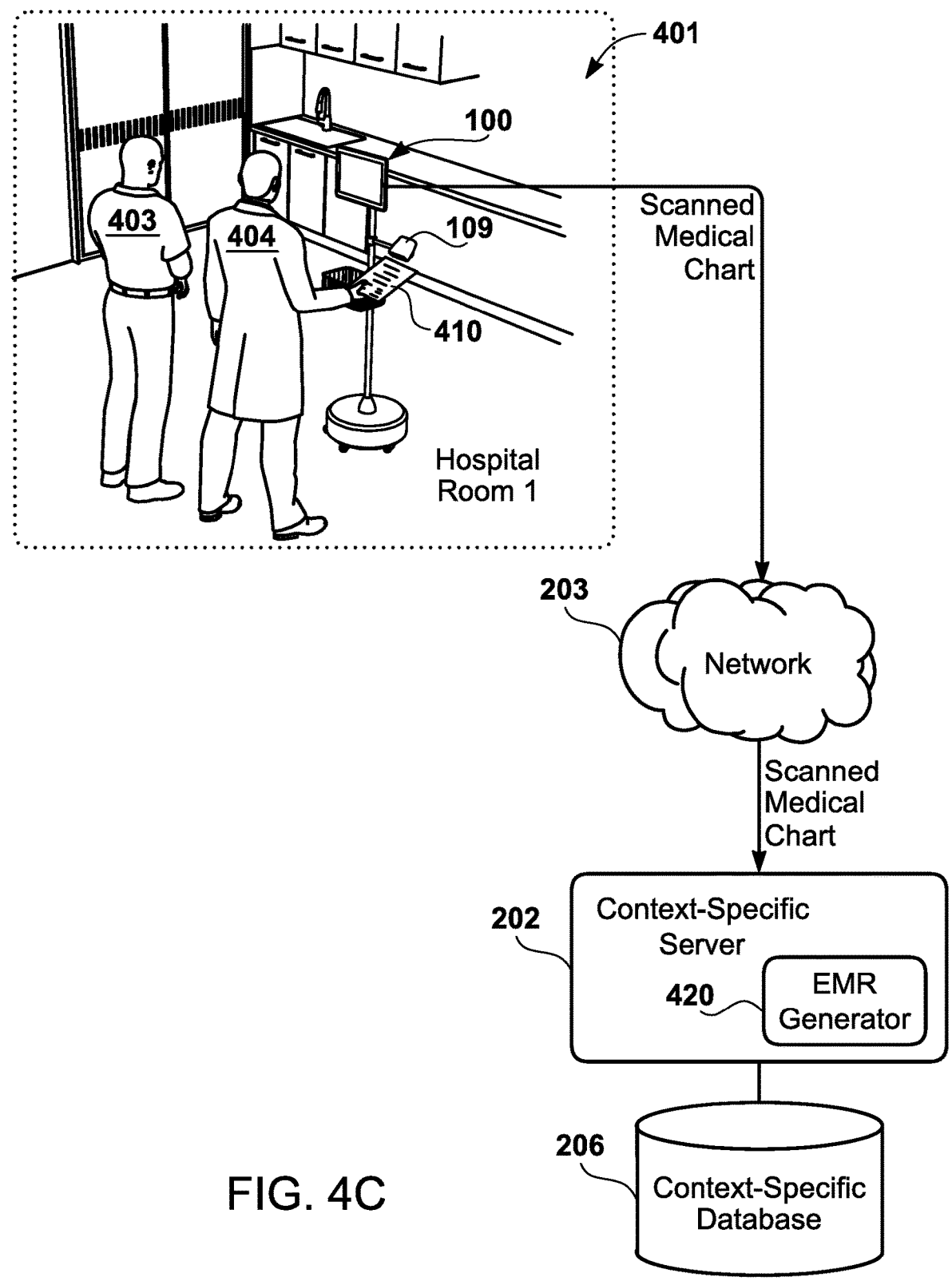
FIG. 4C illustrates an example of the mobile language interpretation platform using the I/O device to scan a medical chart of the first patient in the first hospital room.

Furthermore, FIG. 4C illustrates an example of the mobile language interpretation platform 100 using the I/O device 109 to scan a medical chart 410 of the first patient 403 in the first hospital room 401. For example, the I/O device 104 may be a camera that performs an image capture of the medical chart 410 that the doctor 404 holds in proximity to the I/O device 109. The mobile language interpretation platform 100 may then send the captured image to the context-specific server 202, at which an EMR generator 420 may generate a new medical record for storage in the context-specific database 206, or update a previous medical record previously stored in the context-specific database 206.

Figure 4D:
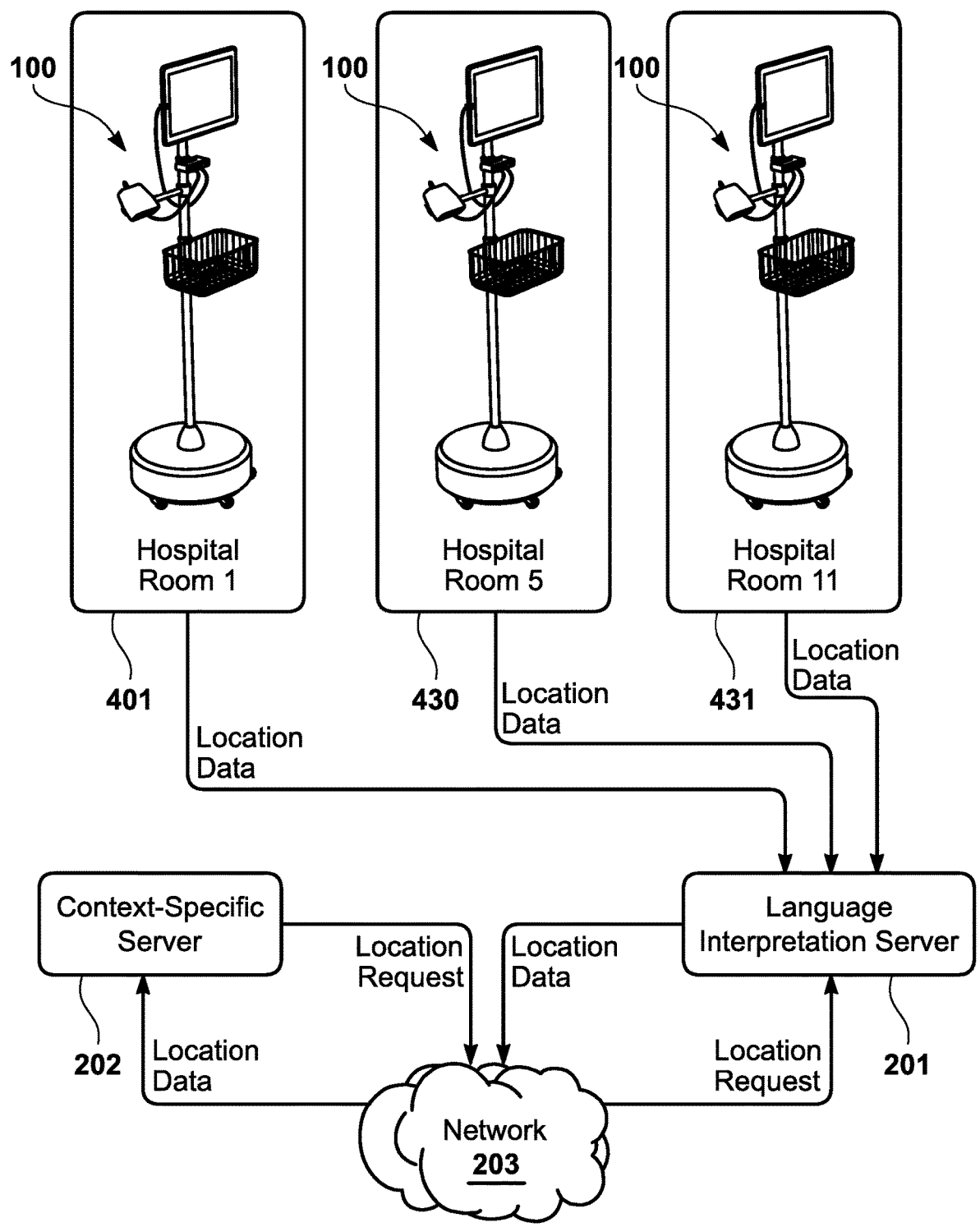
FIG. 4D illustrates a location identification service.

As another example, FIG. 4D illustrates a location identification service. In one embodiment, the context-specific server 202 determines the physical locations of various mobile language interpretation platforms 100 by sending a location request, via the network 203, to the language interpretation server 201. For example, each of the mobile language interpretation platforms 100 may have a sensor 303 in the form of a GPS sensor, and may send corresponding location data to the language interpretation server 201 via a software application. Alternatively, each of the mobile language interpretation platforms 100 may send the sensed data directly to the context-specific server 202. As yet another alternative, the location data may be sent from the sensor 303 without a request (e.g., the sensor 303 may be configured to determine the location at a predetermined time interval).

Figure 4E:
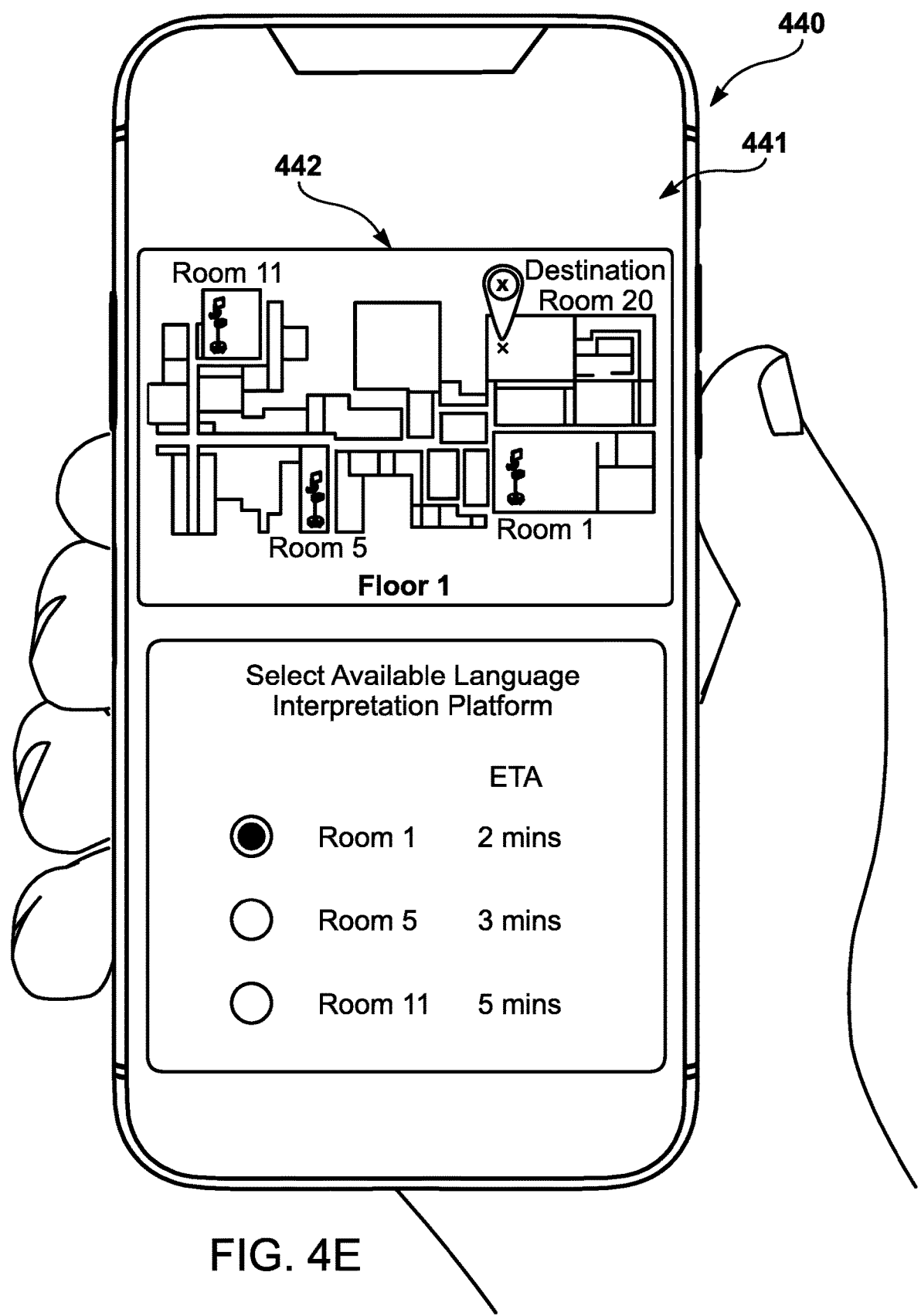
FIG. 4E illustrates a computing device that may be used by an end-user to request mobilization of the mobile language interpretation platforms.
Figure 4F:
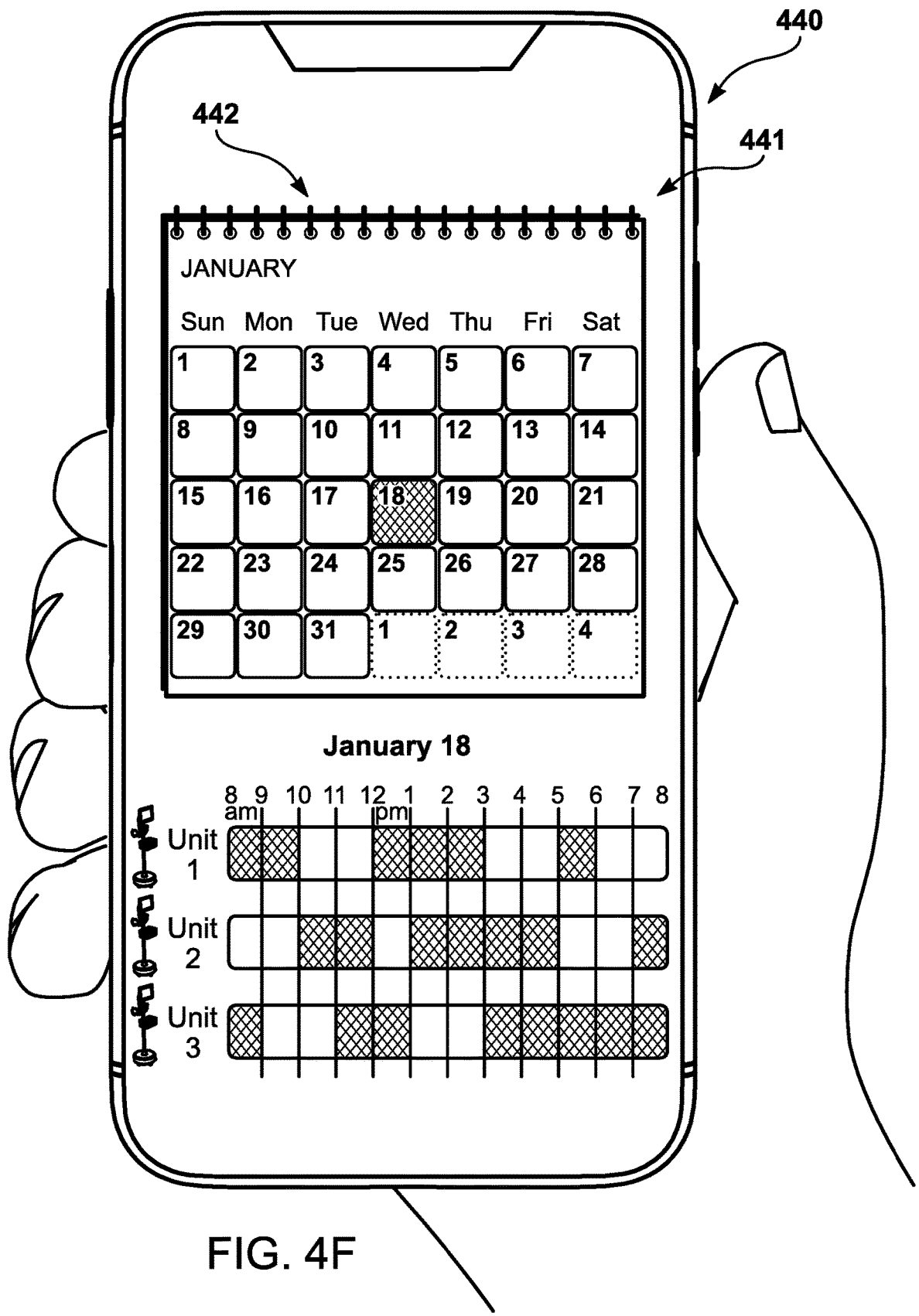
FIG. 4F illustrates the graphical user interface ("GUI") illustrated in FIG. 4E a scheduling configuration.

Furthermore, FIG. 4E illustrates a computing device 440 (e.g., smartphone, tablet device, etc.) that may be used by an end-user to request mobilization of the mobile language interpretation platforms 100. For example, a display screen 441 of the computing device 440 may display a GUI 442 that depicts a virtual map and interactive indicia. The end-user may view the proximity (e.g., identified hospital rooms) of various mobile language interpretation platforms 100 on the virtual map, and may select a mobile language interpretation platform based on the proximity. As another alternative, FIG. 4F illustrates the GUI 442 illustrated in FIG. 4E being utilized for a scheduling configuration. For example, the GUI 442 allows the end-user to reserve a mobile language interpretation platform 100 on a particular day and time; such reservation may allow for manual pick-up or for automated delivery.

Figure 5:
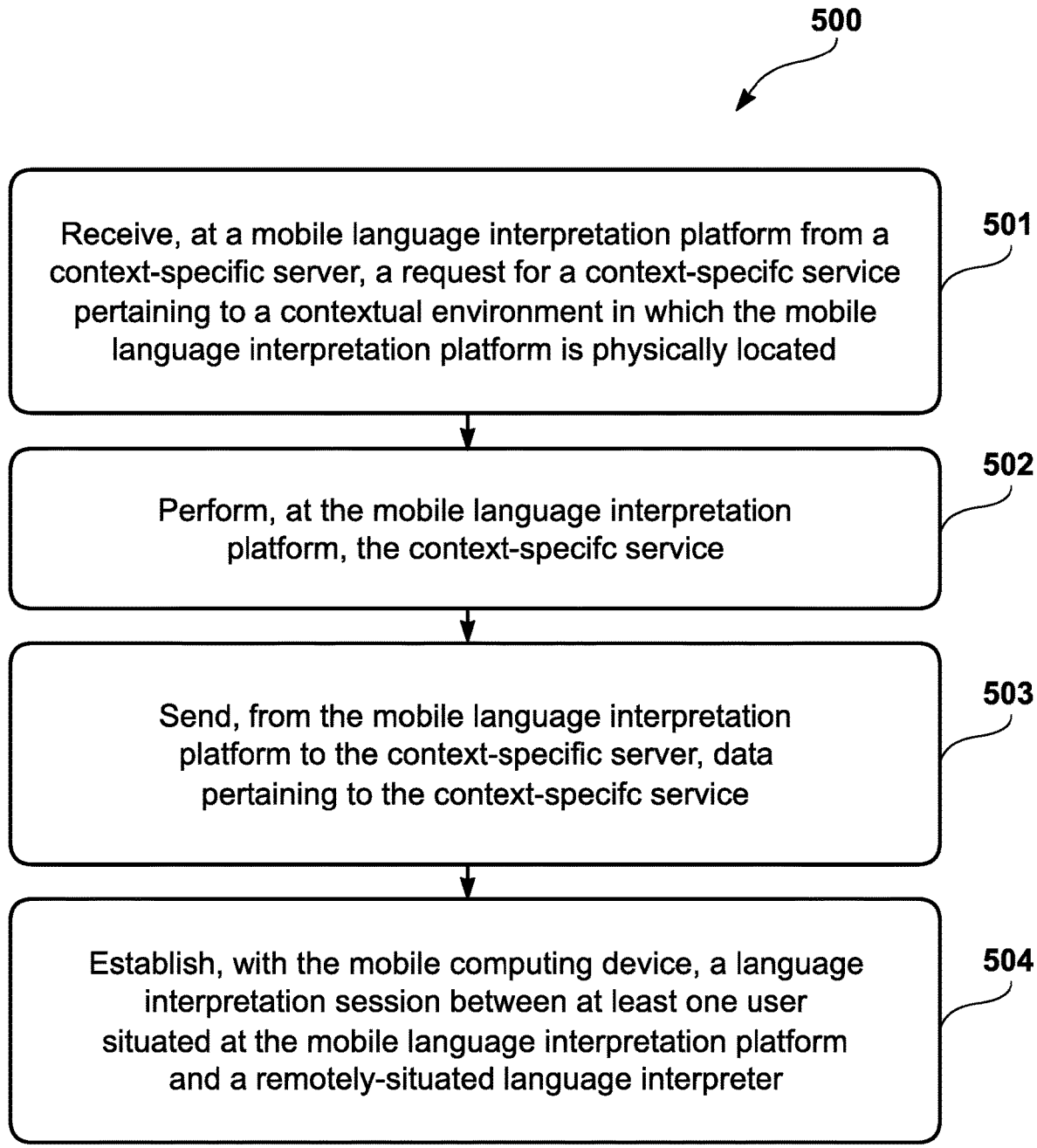
FIG. 5 illustrates a process that may be utilized by the processor illustrated in FIG. 3 to implement the context-specific services illustrated in FIGS. 4A-4F.

FIG. 5 illustrates a process 500 that may be utilized by the processor 301 illustrated in FIG. 3 to implement the context-specific services illustrated in FIGS. 4A-4F. At a process block 501, the process 500 receives, at the mobile language interpretation platform 100 from the context-specific server 202, a request for a context-specific service pertaining to a contextual environment in which the mobile language interpretation platform 100 is physically located. The mobile language interpretation platform has the mobile computing device 101 situated on a mobile support device 104. Further, at a process block 502, the process 500 performs, at the mobile language interpretation platform 100, the context-specific service. Additionally, at a process block 503, the process 500 sends, from the mobile language interpretation platform 100 to the context-specific server 202, data pertaining to the context-specific service. Finally, at a process block 504, the process 500 establishes, with the mobile computing device 101, a language interpretation session between at least one user situated at the mobile language interpretation platform 100 and a remotely-situated language interpreter 205.

It is understood that the apparatuses, systems, computer program products, and processes described herein may also be applied in other types of apparatuses, systems, computer program products, and processes. Those skilled in the art will appreciate that the various adaptations and modifications of the embodiments of the apparatuses, systems, computer program products, and processes described herein may be configured without departing from the scope and spirit of the present apparatuses, systems, computer program products, and processes. Therefore, it is to be understood that, within the scope of the appended claims, the present apparatuses, systems, computer program products, and processes may be practiced other than as specifically described herein.

We claim:

1. A computer program product comprising a computer readable storage device having a computer readable program stored thereon, wherein the computer readable program when executed on a computer causes the computer to:

receive, at a mobile language interpretation platform from a context-specific server, a request for a context-specific service pertaining to a contextual environment in which the mobile language interpretation platform is physically located, the mobile language interpretation platform having a mobile computing device situated on a mobile support device;

perform, at the mobile language interpretation platform, the context-specific service;

send, from the mobile language interpretation platform to the context-specific server, data pertaining to the context-specific service; and automatically establish, with the mobile computing device via an IoT configuration through one or more computer-to-computer interactions without a human user input, a video remote language interpretation session between at least one user situated at the mobile language interpretation platform and a remotely-situated language interpreter.

2. The computer program product of claim 1, wherein the context-specific service is a non-language interpretation service.

3. The computer program product of claim 2, wherein the context-specific service is a rerouting service in which the mobile language interpretation platform autonomously mobilizes from a first location within the contextual environment to a second location with the contextual environment.

4. The computer program product of claim 3, wherein the computer is further caused to send an alert from a sensor operably attached to the mobile language interpretation platform to the context-specific server, the context-specific server generating the request for the context-specific service based on the alert.

5. The computer program product of claim 2, wherein the context-specific service is a user identification service in which a scanner operably attached to the mobile language interpretation platform scans a user identifier in proximity to a user.

6. The computer program product of claim 2, wherein the context-specific service is a record generation service in which a scanner operably attached to the mobile language interpretation platform scans a record in proximity to a user.

7. The computer program product of claim 2, wherein the context-specific service is a location service in which the mobile language interpretation platform sends location data sensed by a location sensor to the context-specific server.

8. The computer program product of claim 2, wherein the context-specific service is a scheduling service in which the mobile language interpretation platform sends scheduling data to a reservation system in operable communication with the context-specific server.

9. The computer program product of claim 1, wherein the computer is further caused to interrupt the language interpretation service to perform the context-specific service.

10. The computer program product of claim 1, wherein the computer is further caused to perform the establishment of the language interpretation service based on the data pertaining to the context-specific service.

11. A method comprising:
receiving, at a mobile language interpretation platform from a context-specific server, a request for a context-specific service pertaining to a contextual environment in which the mobile language interpretation platform is physically located, the mobile language interpretation platform having a mobile computing device situated on a mobile support device;

performing, at the mobile language interpretation platform, the context-specific service;

sending, from the mobile language interpretation platform to the context-specific server, data pertaining to the context-specific service; and automatically establishing, with the mobile computing device via an IoT configuration through one or more computer-to-computer interactions without a human user input, a video remote language interpretation session between at least one user situated at the mobile language interpretation platform and a remotely-situated language interpreter.

12. The method of claim 11, wherein the context-specific service is a non-language interpretation service.

13. The method of claim 12, wherein the context-specific service is a rerouting service in which the mobile language interpretation platform autonomously mobilizes from a first location within the contextual environment to a second location with the contextual environment.

14. The method of claim 13, further comprising sending an alert from a sensor operably attached to the mobile language interpretation platform to the context-specific server, the context-specific server generating the request for the context-specific service based on the alert.

15. The method of claim 12, wherein the context-specific service is a user identification service in which a scanner operably attached to the mobile language interpretation platform scans a user identifier in proximity to a user.

16. The method of claim 12, wherein the context-specific service is a record generation service in which a scanner operably attached to the mobile language interpretation platform scans a record in proximity to a user.

17. The method of claim 12, wherein the context-specific service is a location service in which the mobile language interpretation platform sends location data sensed by a location sensor to the context-specific server.

18. The method of claim 12, wherein the context-specific service is a scheduling service in which the mobile language interpretation platform sends scheduling data to a reservation system in operable communication with the context-specific server.

19. The method of claim 11, wherein the computer is further caused to interrupt the language interpretation service to perform the context-specific service.

20. A mobile language interpretation platform comprising:
a mobile support device;
one or more wheels attached to the mobile support device; and
a computing device operably attached to the mobile support device, the computing device having a receiver that receives, from a context-specific server, a request for a context-specific service pertaining to a contextual environment in which the mobile language interpretation platform is physically located, a processor that performs the context-specific service and automatically establishes, via an IoT configuration through one or more computer-to-computer interactions without a human user input, a video remote language interpretation session between at least one user situated at the mobile language interpretation platform and a remotely-situated language interpreter, and a transmitter that sends data pertaining to the context-specific service to the context-specific server.

* * * * *